United States Patent [19]
McCarthy et al.

[11] Patent Number: 5,883,199
[45] Date of Patent: Mar. 16, 1999

[54] POLYACTIC ACID-BASED BLENDS

[75] Inventors: Stephen P. McCarthy, Tyngsboro; Richard A. Gross, Chelmsford; Wenguang Ma, Lowell, all of Mass.

[73] Assignee: University of Massachusetts, Boston, Mass.

[21] Appl. No.: 825,810

[22] Filed: Apr. 3, 1997

[51] Int. Cl.$^6$ .............................. C08F 20/00; B29D 22/00
[52] U.S. Cl. .................... 525/437; 525/450; 604/212; 604/370; 604/403; 604/408; 428/35.2; 428/35.7; 428/36.92
[58] Field of Search ...................... 525/437, 450; 604/403, 212, 358, 370, 408; 428/34.1, 35.2, 35.7, 36.92

[56] References Cited

U.S. PATENT DOCUMENTS

| | | | |
|---|---|---|---|
| 4,095,600 | 6/1978 | Casey et al. ............................. | 525/437 |
| 5,216,050 | 6/1993 | Sinclair ................................... | 524/108 |
| 5,252,642 | 10/1993 | Sinclair et al. ......................... | 524/108 |
| 5,685,540 | 11/1997 | Kakizawa ............................... | 525/444 |

FOREIGN PATENT DOCUMENTS 96-231837  2/1995  Japan .

OTHER PUBLICATIONS

Cai et al., "Effects of Physical Aging, Crystallinity, and Orientation on the Enzymatic Degradation of Poly(Lactic acid)", *J. Polymer Science*, 34:2701–2708 (1996).

Gajria et al., "Miscibility and biodegradability of blends of poly(lactic acid) and poly(vinyl acetate)", *Polymer*, 37:437–444 (1996).

Sheth et al., "Biodegradable Polymer Blends of Polylactic Acid (PLA) and Polyethylene Glycol (PEG)", *ANTEC '95*, 1829–1833 (1995).

Younes et al., Phase Separation in Poly(Ethylene Glycol)/Poly(Lactic Acid) Blends, *Polym. J.*, 24(8):765–773 (1988).

*Primary Examiner*—Nathan M. Nutter
*Attorney, Agent, or Firm*—Fish & Richardson P.C.

[57] ABSTRACT

Biodegradable blends including a first, polylactic acid-based polymer or copolymer, and a second polymer or copolymer including one or more polyesters, e.g., an aliphatic polyester or a polyester of one aliphatic $C_2$ to $C_{20}$ diacid or of a combination of two more different aliphatic $C_2$ to $C_{20}$ diacids, wherein the first and second polymers are present in a ratio of 9:1 to 1:9, are described.

25 Claims, 7 Drawing Sheets

POLYACTIC ACID-BASED BLENDS

STATEMENT AS TO FEDERALLY SPONSORED RESEARCH

Funding for the work described herein was partially provided by the National Science Foundation under grant number EEC-9314562. The Government has certain rights in the invention.

BACKGROUND OF THE INVENTION

The invention relates to polylactic acid-based blends.

Succinic acid and diols can form biodegradable aliphatic polyesters and copolyesters through coupling and polycondensation reactions. The main unit structure resulting from these reactions is:

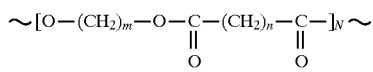

Examples of biodegradable aliphatic polyesters and copolyesters having the unit structure shown above are polybutylene succinate (PBSU), where m is 4 and n is 2, polyethylene succinate (PESU), where m is 2 and n is 2, a random copolymer of polybutylene succinate adipate (PBSU-AD) where m is 4 and n is 2 or 4, and polyethylene succinate adipate (PESU-AD) where m is 2 and n is 2 or 4.

These polyesters and copolyesters have interesting properties including biodegradability, melt processability, and thermal and chemical resistance. One of these, BIONOLLE®, a commercially available aliphatic succinate-adipate polyester, has excellent physical properties. For example, the thermal resistance of BIONOLLE is equivalent to that of polyethylene, but the yield strength is higher than polyethylene. The stiffness of BIONOLLE is between high density and low density polyethylene (LDPE). Particularly for BIONOLLE #3000, its impact strength is equivalent to that of LDPE, while its elongation at break is higher than that of LDPE.

Polylactic acid can be made from lactic acid (lactate). Lactic acid is a natural molecule that is widely employed in foods as a preservative and a flavoring agent. It is the main building block in the chemical synthesis of the polylactide family of polymers. Although it can be synthesized chemically, lactic acid is procured principally by microbial fermentation of sugars such as glucose or hexose. These sugar feed stocks can be derived from potato skins, corn, and dairy wastes. The lactic acid monomers produced by fermentation are then used to prepare polylactide polymers.

Lactic acid exists essentially in two stereoisomeric forms, which give rise to several morphologically distinct polymers: D-polylactic acid, L-polylactic acid, D,L-polylactic acid, meso-polylactic acids and any combinations of thereof. D-polylactic acid and L-polylactic acid are stereoregular polymers. D,L-polylactic acid is a racemic polymer obtained from a mixture of D- and L-lactic acid, and meso-polylactic acid can be obtained from D,L-lactide. The polymers obtained from the optically active D and L monomers are semicrystalline materials, but the optically inactive D,L-polylactic acid is amorphous.

Lactic acid has a hydroxyl group as well as a carboxylic group, and hence can be easily converted into a polyester. These polyesters have some potential advantages when compared to other biodegradable polymers such as polyhyroxybutyrate and polycaprolactone, as to their strength, thermoplastic behavior, biocompatibility, and availability from renewable sources, and have been classified as "water sensitive," because they degrade slowly compared with "water soluble" or "water swollen" polymers. However, while polylactic acid is a biodegradable polymer with generally good processability, it is brittle, and the brittleness increases with time due to physical aging, i.e., densification of the polymer at a molecular level.

SUMMARY OF THE INVENTION

The invention is based on the discovery that polylactic acid (PLA)-based polymers or copolymers and polymers or copolymers of polyesters, e.g., polybutylenesuccinate, polybutylene succinate-adipate or polybutylene succinate-terephthalte (wherein the diacids of the polyester would be, for example, succinic acid, adipic acid, terephthalic acid, or any combinations thereof), can be used to make new biodegradable blends that, compared to PLA, have superior tensile and mechanical properties such as stiffness, toughness, and elongation to break, as well as excellent biodegradability and aging properties.

In general, the invention features a biodegradable blend including a first, polylactic acid-based polymer or copolymer, and a second polymer or copolymer including one or more polyesters, e.g., an aliphatic polyester or a polyester of one aliphatic $C_2$ to $C_{20}$ diacid or of a combination of two more different aliphatic $C_2$ to $C_{20}$ diacids, wherein the first and second polymers are present in a ratio of 9:1 to 1:9, by weight, e.g., 5:1 to 1:5, or 2:1 to 1:2, or 1:1. For example, the first polymer can be a homopolymer of polylactic acid, e.g., D-polylactic acid, L-polylactic acid, D,L-polylactic acid, meso-polylactic acid, and any combination of D-polylactic acid, L-polylactic acid, D,L-polylactic acid and meso-polylactic acid. In addition, the first polymer can be a copolymer having at least 50, 60, 70, or more, up to 100 percent, by weight, of polylactic acid.

The second polymer or copolymer can be, for example, a polybutylenesuccinate homopolymer, polybutyleneadipate homopolymer, polybutylenesuccinate-adipate copolymer, polyethylenesuccinate homopolymer, polyethyleneadipate homopolymer, or a polyethylenesuccinate-adipate copolymer, or a copolyester of an aliphatic polyester and up to 50 percent, by weight, of an aromatic polyester, such as terephthalate, as long as the overall copolyester (and second polymer) is biodegradable.

The blend can further include a compatibilizer including one or more polyesters, polyethers, or polyvinyl alcohols.

The new biodegradable blends have an elongation at break of at least 10 percent, for example, at least 50, 100, 200, 300, 400, and up to 500 percent or more. The blends also have an elongation at break of at least 10 percent, e.g., 50, 100, 200, 300, 400, and up to 500 percent or more after 70 days of aging. In addition, the blends have a toughness of at least 10 $MJ/m^3$, e.g., 20, 40, 60, and up to 120 $MJ/m^3$ or more.

The second polymer can be present in the new biodegradable blends as a co-continuous phase with the first polymer, and at least the first or the second polymer or copolymer is present in a continuous phase in the blend.

The first, polylactic acid-based polymer or copolymer can be a homopolymer of lactic acid or a block, graft, or random copolymer of lactic acid having the general formula:

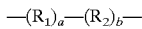

wherein $R_1$ is a lactic acid unit, $R_2$ is caprolactone, glycolide, trimethylene carbonate, dioxanone, butyryl lactone, or ethylene oxide, a is 10 to 10,000, e.g., 100 to 7,500, or 1000 to 5000, and b is 0 to 10,000, e.g., 100 to 7,500, or 1000 to 5000.

The polyester of the second polymer or copolymer can have the formula:

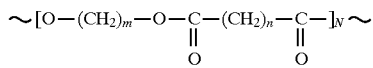

wherein m is 2 to 20, e.g., 4, 8, or 12; n is 2 to 20, e.g., 2 and 4, or 6, or 8; and N is 10 to 10,000, e.g., 500, 3,500, or 5000.

The new biodegradable blends can include the first, polylactic acid-based polymer or copolymer as a polylactic acid homopolymer, and the second polymer or copolymer as a polybutylenesuccinate homopolymer, polybutyleneadipate homopolymer, polybutylenesuccinate-adipate copolymer, polyethylenesuccinate homopolymer, polyethyleneadipate homopolymer, or a polyethylenesuccinate-adipate copolymer.

In another embodiment, the invention features articles manufactured from the new biodegradable blends. For example, the invention features sheets or films, bags, containers, such as bottles and disposable cups, disposable diapers, and other items including the new blends.

A "polylactic acid-based polymer or copolymer" is a homopolymer or a copolymer having at least 50% by weight of polylactic acid. As used herein, the term "polylactic acid," without further designation, includes any one or more of four morphologically distinct polylactic acid polymers: D-polylactic acid, L-polylactic acid, D,L-polylactic acid, and meso-polylactic acid. "D-polylactic acid" and "L-polylactic acid" are dextro-polylactic acid and levo-polylactic acid, respectively, and both of them are optically active polymers that rotate a light vector when transmitted through the polymer. "D,L-polylactic acid" is a racemic polymer, i.e., a copolymer of D-polylactic acid and L-polylactic acid having a well-defined conformation of D- and L-polylactic acid units. "Meso-polylactic" is a random copolymer of D-polylactic acid and L-polylactic acid. An "aliphatic polyester of a diacid and a diol" is a polyester formed by the reaction of a diacid and a diol.

The invention provides several advantages. Polylactic acid by itself is a brittle material having poor toughness and low elongation to break, and these properties worsen with time due to its physical aging behavior. Furthermore, the biodegradability of polylactic acid is slow. The new blends overcome these deficiencies of polylactic acid. Moreover, the new blends are environmentally friendly and commercially attractive for making biodegradable plastic films, sheets, and other plastic products made by conventional processing methods such as blown film, extrusion, and injection molding. These plastic products can be used for food packaging, compost bags, and other disposable items. The new blends provide an entry for polylactic acid in the potentially large market of biodegradable polymers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples described herein are illustrative only and not intended to be limiting.

Other features and advantages of the invention will be apparent from the following detailed description, and from the claims.

DETAILED DESCRIPTION

Figure 1:
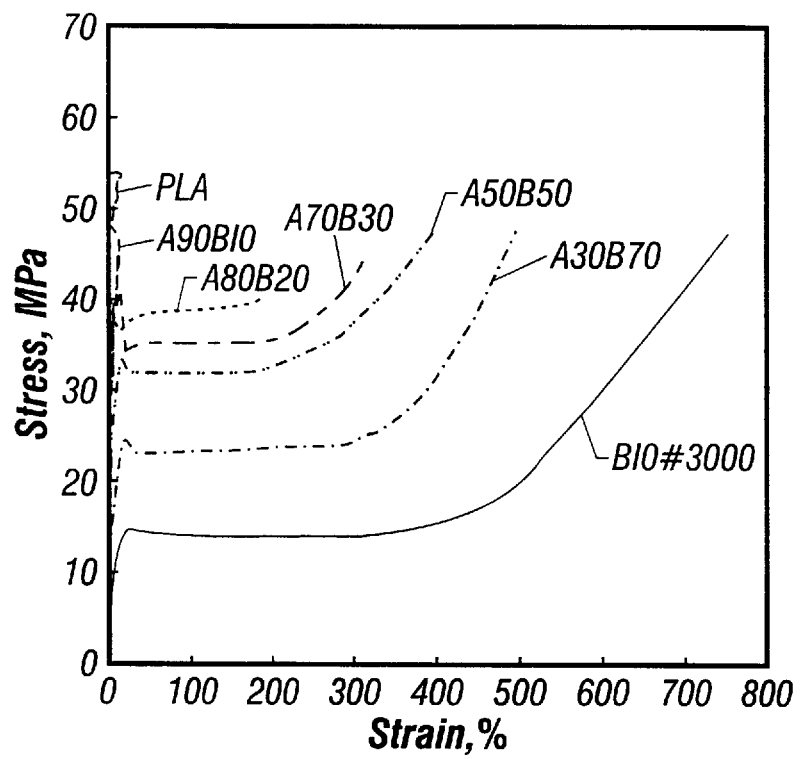
FIG. 1 is a graph showing complete stress-strain curves of polylactic acid, BIONOLLE#3000, and their blends.

Polylactic acid-based polymers and polymers of polyesters, e.g., aliphatic polyesters of diols and diacids, can be used to make new blends that have surprisingly good mechanical and biodegradable properties compared to polylactic acid alone. The new blends provide tough, biodegradable plastics that can be used to make biodegradable plastic films, sheets, and other products made by conventional blown film, extrusion, and injection molding processing methods. These plastic products can be used for food packaging, compost bags, and other disposable items.

Compared to polylactic acid, the new blends provide a large increase in elongation (e.g., from 5% to 500%), toughness enhancement (from less than 10 MJ/m$^3$ to more than 120 MJ/m$^3$), and increased biodegradation rate. The modulus of these blends decreases with increasing amount of the aliphatic polyester, i.e., Bionolle#3000 (from 1.3 GPa of polylactic acid to 0.3 GPa of Bionolle#3000), and elongation to break increases with increasing amount of the aliphatic polyester (e.g., from 5% to 500%). The blends with more than 20% by weight of Bionolle#3000 possess toughness of more than 70 MJ/m$^3$, more than 200% elongation at break and other excellent tensile properties, which are retained even after the blends have aged for 70 days in the temperature range of −15° to 60° C. Compared to polylactic acid, these blends also have a relatively high degradation rates in soil and composting environment.

Materials

The main components needed to make the new blends are polylactic acid-based polymers and polyesters, e.g., aliphatic polyesters of diols and diacids. Optionally, a compatibilizer may be added to the blends.

The simplest polylactic acid-based polymer is polylactic acid, which can be obtained from, e.g., Cargill Inc. (EcoPla Division, Minnesota). The polylactic acid used for the experiments described herein had an 8% meso content (96% L) and a number average molecular weight of 70,100. Other polylactic-based polymers can also be used to make the new tough blends with aliphatic polyesters of diols and diacids.

For example, a polylactic-based polymers can be either a homopolymer of lactic acid or a block, graft, or random copolymer of lactic acid having the general formula:

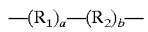

wherein $R_1$ is a lactic acid unit and $R_2$ is caprolactone, glycolide, trimethylene carbonate, dioxanone, butyryl lactone, or ethylene oxide. When the polylactic acid-based polymer is a homopolymer, the b term is zero in the general formula.

Commercially available aliphatic polyesters of diols and diacids include the BIONOLLE family of polymers, e.g., BIONOLLE #1000, #2000, #3000, #6000, and #7000, which can be obtained from, e.g., Showa Highpolymer Co., Ltd, Japan. Bionolle #3000, #6000, and #7000, which have molecular weights ($M_w$) of 23,300, 250,000 and 270,000, respectively, and melting points of about 91°, 102°, and 89° C., respectively, were used to make the new blends which were tested as described below. Other aliphatic polyesters of diols and diacids can also be used.

Examples of diols in the aliphatic polyesters include any aliphatic diols including ethylene glycol and 1,4-butanediol. Examples of diacids in the aliphatic polyesters include any individual diacids or combinations of two or more aliphatic diacids, in the range of $C_2$ to $C_{20}$, in a weight percent from 0 to 100, e.g., oxalic acid, malonic acid, succinic acid, glutaric acid, adipic acid, n-butylmalonic acid, succinic acid, azelaic acid, sebacic acid, ethyl diethylmalonate and dibutyl succinate. Specific aliphatic polyesters include polybutylene succinate (PBSU), polyethylene succinate (PESU), random copolymers of polybutylene succinate adipate (PBSU-AD), and polyethylene succinate adipate (PESU-AD).

Among other features of the aliphatic polyesters used in the new blends are that these polyesters are biodegradable and that they impart ductility to polylactic acid-based polymers by forming a continuous or co-continuous phase in the morphology of the blends. The polylactic acid-based polymers and the aliphatic polyesters are immiscible, but synergistically compatible in the blends, i.e., the properties of the blends are greater than that of the mixtures of polylactic acid-based polymer and aliphatic polyester determined by the additive rule of mixture. The range of weight average molecular weights of the polylactic acid-based polymer and the aliphatic polyester that can be used is 5,000 to a million, for example 10,000 to 500,000 or 15,000 to 250,000. The range of melting points of the polylactic acid-based polymer and aliphatic polyester that can be used is 50° to 300° C., for example 60 to 200° C., e.g., 80° to 150° C.

Besides a purely aliphatic polyester of diols and diacids, a copolyester of an aliphatic polyester and an aromatic polyester can be used so long as the copolyester is biodegradable and imparts ductility to polylactic acid-based polymers. An example of an aromatic polyester that can be used (in up to 50 percent by weight) in the copolyester is polyethylene terephthalate. Other aromatic polyesters can be used.

Examples of compatibilizers include AB block or AB graft copolymers that consist of a polylactic acid-based polymer or a polymer which is miscible with the polylactic acid-based polymers, and an aliphatic copolyester of polymers based on diols and diacids or polymers which are miscible with these aliphatic copolyesters. These compatibilizers can be added to the blend in an amount ranging from, e.g., 0.1 to 10 percent, e.g., 2, 3, or 5 percent.

Preparing Polylactic-Based Polymer Blends

Standard melt processing equipment and processing conditions can be used to prepare the new blends. Examples of polymer melt processing equipment that can be used to make the new blends include melt mixers (Banbury mixer), blenders, extruders for sheet, film, profile and blown-film extrusion, vulcanizers, calenders, and spinnerets for fiber spinning, molding, and foaming.

The polylactic acid-based polymers and the polymers or copolymers of polyesters were carefully dried at 40° C. under vacuum for at least 24 hours to minimize hydrolytic degradation of polylactic acid-based polymer during the subsequent melt processing. Blending was done on a single screw extruder operating between 150° and 160° C. and a screw speed of 50 rpm. Each sample was extruded twice. This protocol can be varied as long as the polymers and polyesters form a continuous or co-continuous phase blend.

The composition and sample code for each blend made up of polylactic acid and BIONOLLE are reported in Table 1. The A in each sample code refers to the percentage of polylactic acid-based polymer in the blend, and the B refers to the polyester, BIONOLLE#3000, BIONOLLE#6000, or BIONOLLE#7000, which were used to make the new blends with polylactic acid.

TABLE 1

| Sample Code | PLA | A90B10 | A80B20 | A70B30 | A50B50 | A30B70 | Bio#__ |
|---|---|---|---|---|---|---|---|
| PLA wt % | 100 | 90 | 80 | 70 | 50 | 30 | 0 |
| BIONOLLE wt % | 0 | 10 | 20 | 30 | 50 | 70 | 100 |

Sample Preparation

Rectangular shaped samples of each blend were prepared to enable uniform testing of characteristics. The tensile test samples were made according to a modified specification in ASTM D 882. In particular, samples of about 0.3 mm thickness, 12.7 mm width, and 38.1 mm length between the grips of the tensile test machine holding the sample, i.e., gage length, were compression molded at 155° C. and cooled in a cooling press machine at 20° C. and 700 psi. Thin film samples were made by melt blending on an extruder and then compression molding to 0.3 mm thickness. The films were cut into 20 mm×20 mm samples for testing biodegradation in soil and in composting environments.

Testing Methods

Tensile test properties of blends were obtained 1, 2, 4, 7, 14, 21, 35, 40, and 70 days after making the samples. During this interim time period between making and testing, the samples were physically aged at room temperature and atmospheric pressure. The tensile test was done according to ASTM D 882 with the following modifications. The grip separation used was 38.1 mm (1.5 inches) instead of 50 mm (2 inches), and the grip separation rate was 2 inches/minute even for samples with elongation at break greater than 100%, while ASTM D 882 specifies that the grip separation rate be 20 inches/minute for samples with elongation at break greater than 100%.

Biodegradation testing in an artificial soil environment was performed on films of the blends using the respirometric method developed at the NSF Biodegradable Polymer Research Center, University of Massachusetts Lowell and designated UML-7645. This test method covers the determination of the degree and rate of aerobic biodegradation of synthetic plastic materials (including formulation additives) in contact with moist soil under controlled laboratory condition. Carbon dioxide production, as a fraction of the measured theoretical carbon content of the test materials, is reported as a function of time. The test is designed to determine the biodegradability of plastic materials, relative to that of a comparative standard material, in an aerobic environment. The test applies to all plastic materials that do not inhibit bacteria and fungi present in soil.

Biodegradation testing in an artificial compost environment was conducted on film samples in a simulated municipal compost as described in Example 4.

In addition, morphology of the blends was observed under polarizing optical and scanning electron microscopy.

Uses of Polylactic Acid-Based Blends

Like wood and paper, these blends are stable in the atmosphere but biodegradable in compost, in moist soil, in water with activated sludges, and in the sea, where a large number of microorganisms are present. These blends can be incinerated with only slight damage to the furnace since the heat of combustion is relatively low, and no toxic gases are generated. The blends made by this invention can be used to make biodegradable plastic film, sheets, and other products by conventional processing methods such as blown film, extrusion, and injection molding methods. The resulting blends can be used to manufacture bags, food packaging, laminated papers, food trays, fishing line, net, rope, diapers, disposable medical supplies, sanitary napkins, shampoo, drug, cosmetic, and beverage bottles, cutlery, brushes, combs, molded and extruded foamed articles such as packing material and cups, and cushions for flexible packing. These blends provide not only the excellent processibility of polyethylene, but also posses excellent properties like those of polyethylene terephthalate. In addition, these blends can be processed into films that are heat-sealable, unlike polyethylene terephthalate.

EXAMPLES

The following examples further describe the invention without limitation.

Example 1

Tensile Testing

The tensile test was done according to ASTM D 882 with the modifications in the sample length between grip separation and the grip separation rate, as stated above. Specifically, tensile testing was done by using an Instron Tensile machine, model 1137, at grip separation rates of 0.5 and 2.0 inches/minute.

Tensile test properties of blends were obtained 1, 2, 4, 7, 14, 21, 35, 40, and 70 days after making the samples. During this interim time period between preparing and testing, the samples were physically aged at room temperature and atmospheric pressure.

The stiffness of the blends was determined from the slope of the initial linear portion of the stress-strain curve. Stress was measured as the nominal stress defined as force per unit original area. Strain and elongation are used as synonymous terms, and they were measured as percent change in length per unit length of a sample. The yield point of the blends, i.e., where a large inelastic deformation starts (yielding occurs), but the material continues to deform and absorb energy long beyond that point, was characterized as the intersection of the initial linear portion of the stress-strain curve and the flat horizontal portion of the stress-strain curve.

The toughness of the blends, which can be defined as the tensile energy to break according to ASTM D 822, was measured according to ASTM D 822 by integrating the area under the stress-strain curve.

Specifically, a load range such that a specimen would fail within its upper two thirds was selected. The cross sectional area of the specimen at several points along its length was measured to an accuracy of 0.0025 mm. The initial grip separation was at 38.1 mm. The rate of grip separation rate was set at 0.5 inches/minute for samples with less than 20% elongation at break, and at 2 inches/minute for samples with more than 20% elongation at break. The load cell of the Instron tester was balanced, zeroed, and calibrated for measuring and recording force. The rectangular test specimen was placed in the grips of the Instron testing machine, taking care to align the long axis of the specimen with an imaginary line joining the points of attachment of the grips to the machine. The grips were tightened evenly and firmly to the degree necessary to minimize slipping of the specimen during test. The Instron machine was started and stress versus grip separation was recorded.

Tensile stress (nominal) was calculated by dividing the load by the original minimum cross-sectional area of the specimen in the loading direction. The modulus value was determined from the initial slope of the stress-strain curve. Tensile strength (nominal) at break was calculated in the same way as tensile stress except that the load at break was used in place of the maximum load. Percentage elongation at break was calculated by dividing the extension (i.e., grip separation) at the moment of rupture of the specimen by the initial length of the specimen between the grips. Yield stress and percentage elongation at yield were determined by recording the stress and percent elongation at the yield point, which was established as noted above.

Figure 2:
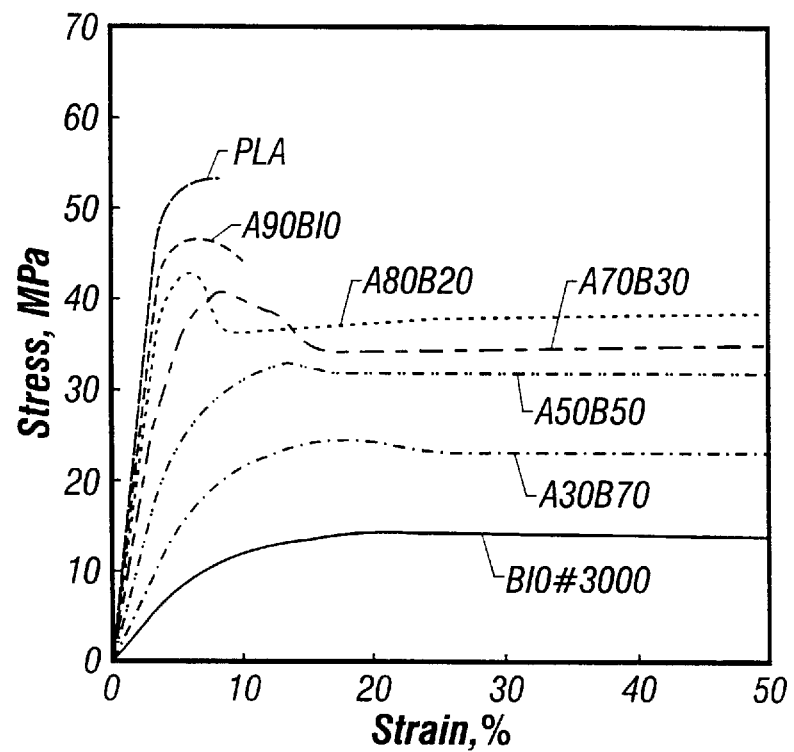
FIG. 2 is a graph showing stress-strain curves of polylactic acid, BIONOLLE#3000, and their blends in the strain range of 0 to 50%.
Figure 3:
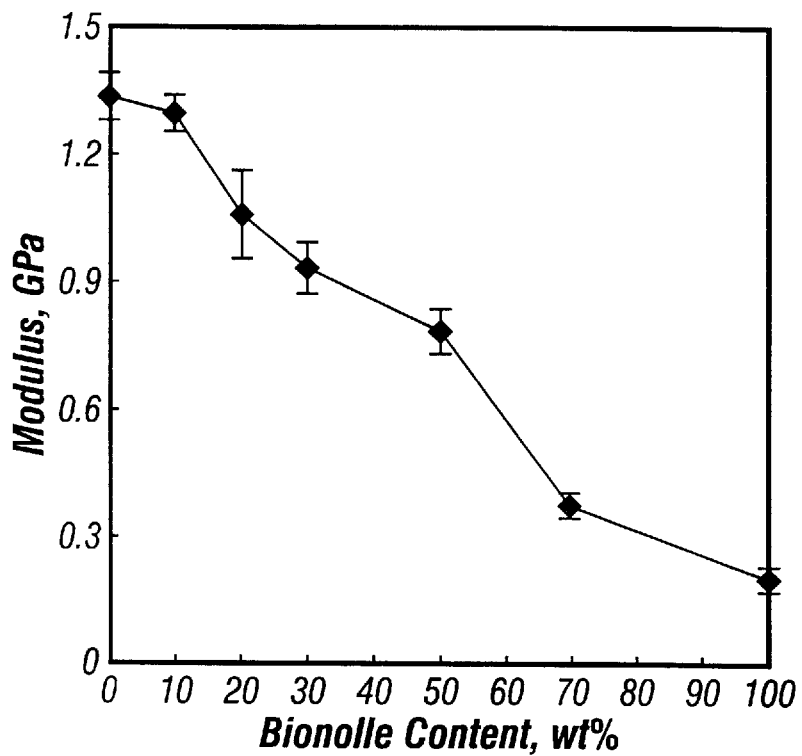
FIG. 3 is a graph showing stiffness (modulus) of polylactic acid, BIONOLLE#3000, and their blends.
Figure 4:
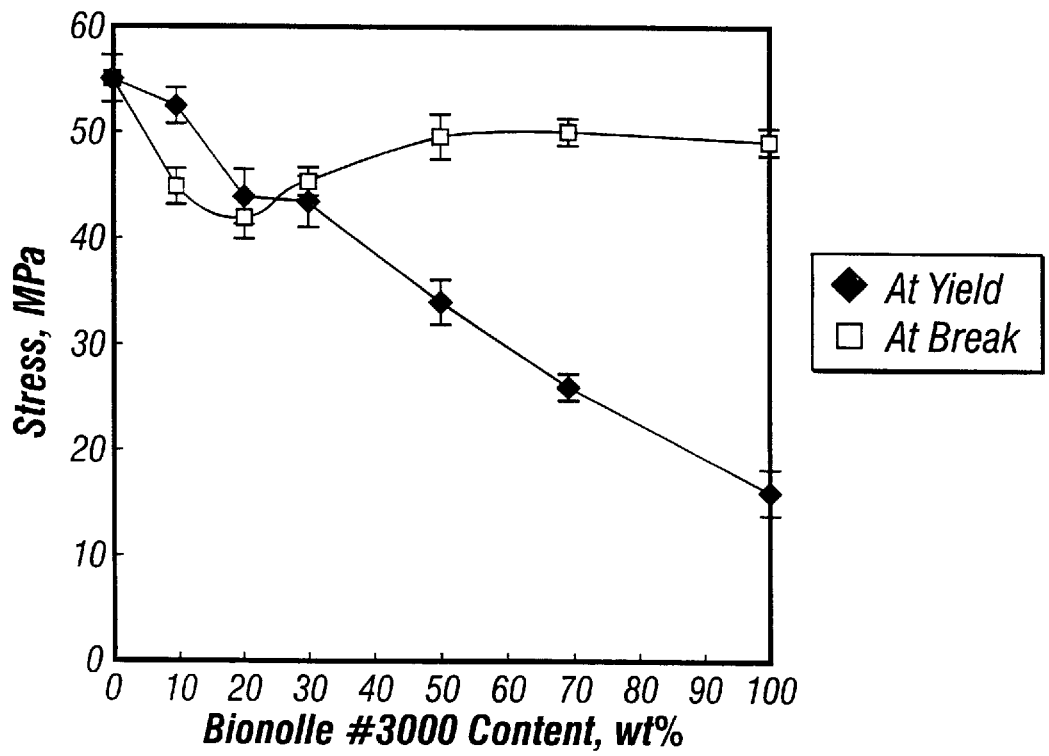
FIG. 4 is a graph showing stress at yield and break of polylactic acid, BIONOLLE#3000, and their blends.

Tensile stress-strain curves of blends of BIONOLLE#3000 and polylactic acid are shown in FIGS. 1 and 2. These blends were aged for 14 days. FIG. 1 shows the complete stress-strain curves of samples coded in Table 2 as PLA, A90B10, A80B20, A70B30, A50B50, A30B70, and BIO#3000. FIG. 2 is a expanded view of the initial portion of the stress-strain curves in FIG. 1, i.e., up to a strain of 50%. The excellent strain hardening characteristics of these blends is exhibited in FIG. 1 by the rapid increase in stress prior to break. For example, strain hardening in A30B70 occurred in the strain range of 300–500%, and the corresponding increase in stress was from about 25 MPa to about 50 MPa.

FIG. 2 shows that both stiffness and stress at yield decrease with increasing BIONOLLE#3000 content, while elongation at yield and at break increase with increasing BIONOLLE#3000 content Based on the data in FIGS. 1 and 2, FIGS. 3 and 4 show modulus (i.e., stiffness) and stress at yield and break, respectively. The outstanding strain hardening behavior of these blends was further exemplified by the increasing difference in stress at break and stress at yield with increasing BIONOLLE#3000 content.

Figure 5:
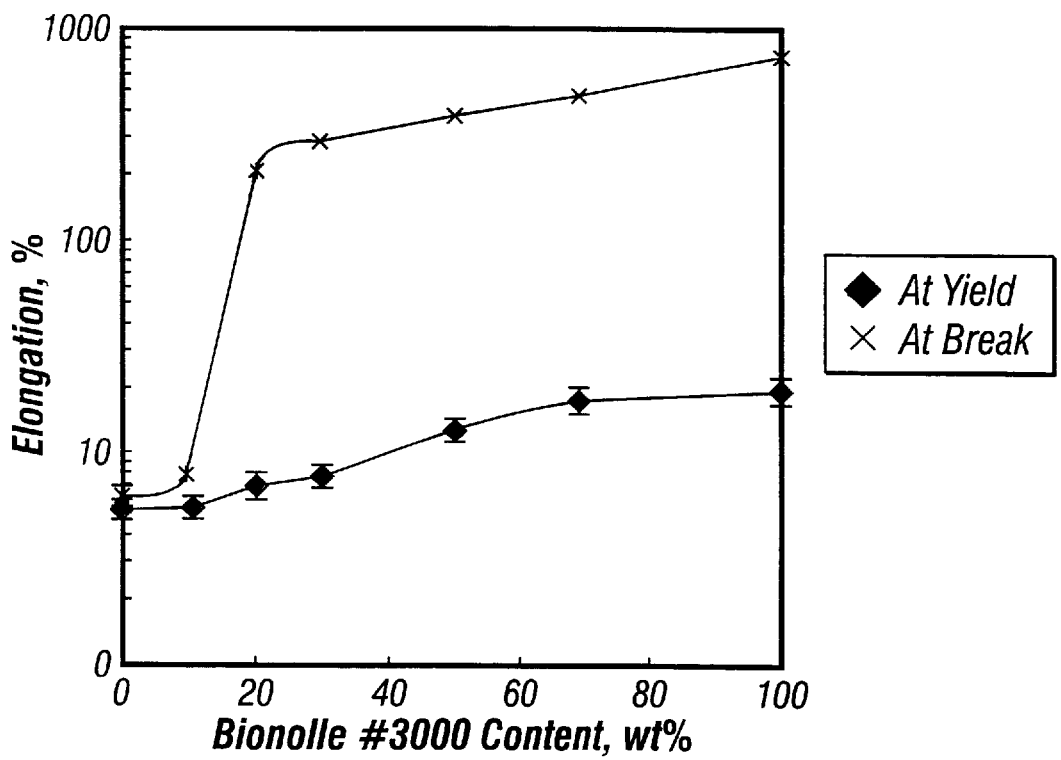
FIG. 5 is a graph showing percent elongation at yield and break of polylactic acid, BIONOLLE#3000, and their blends.
Figure 6:
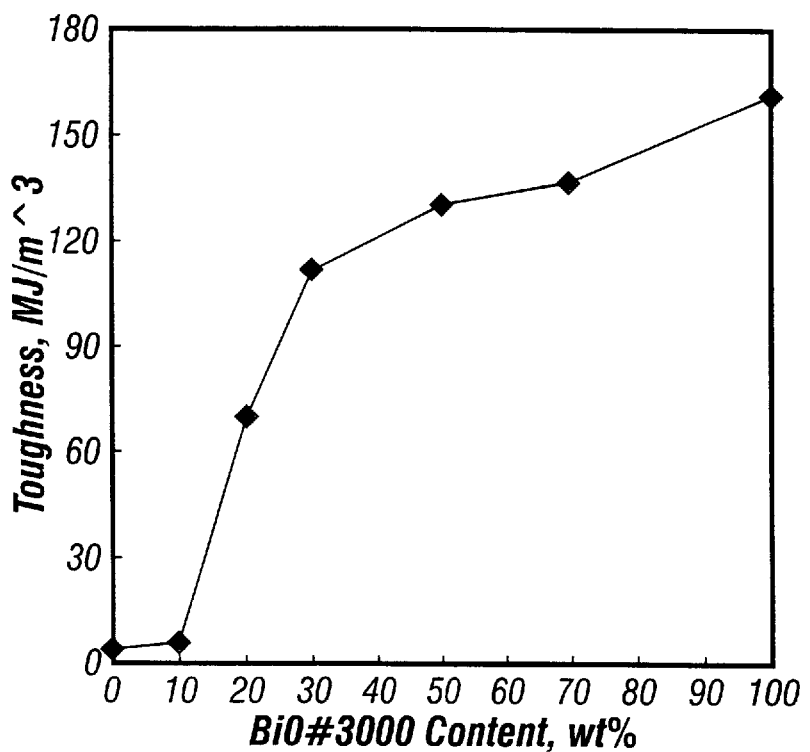
FIG. 6 is a graph showing toughness of polylactic acid, BIONOLLE#3000, and their blends.

FIG. 5 shows that the elongation at both yield and break of polylactic acid/BIONOLLE#3000 blends increase with BIONOLLE#3000 content, with a dramatic increase at break above 10 percent BIONOLLE. FIG. 6 shows that the toughness of polylactic acid/BIONOLLE#3000 blends increases as a function of BIONOLLE#3000 content above 10 percent. Both FIGS. 5 and 6 show a surprising and unexpected increase in the elongation at break of the blends when the BIONOLLE#3000 content was increased to over about 10 weight percent to about 30 weight percent in the polylactic acid/BIONOLLE#3000 blends, and in toughness of the blends when the BIONOLLE#3000 content was increased to over about 10 eight percent to about 40 or 50 weight percent in the polylactic acid/BIONOLLE#3000 blends.

Figure 7:
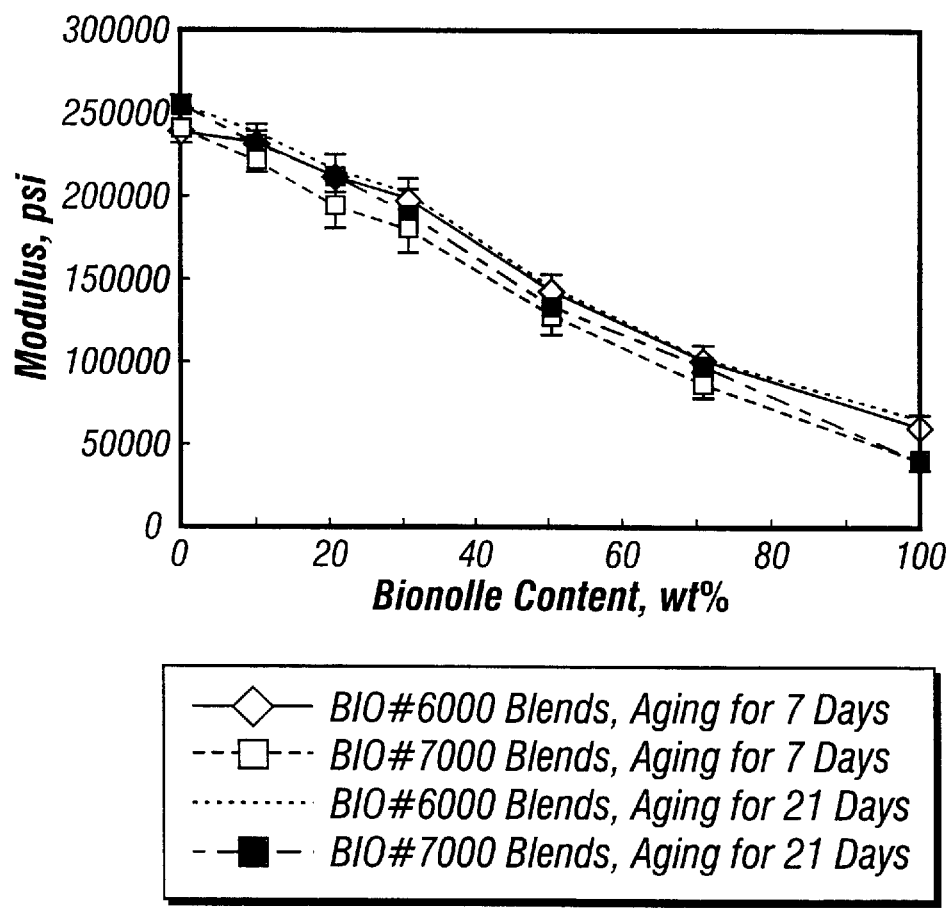
FIG. 7 is a graph showing stiffness (modulus) of polylactic acid, BIONOLLE#6000, BIONOLLE#7000, and their blends.
Figure 8:
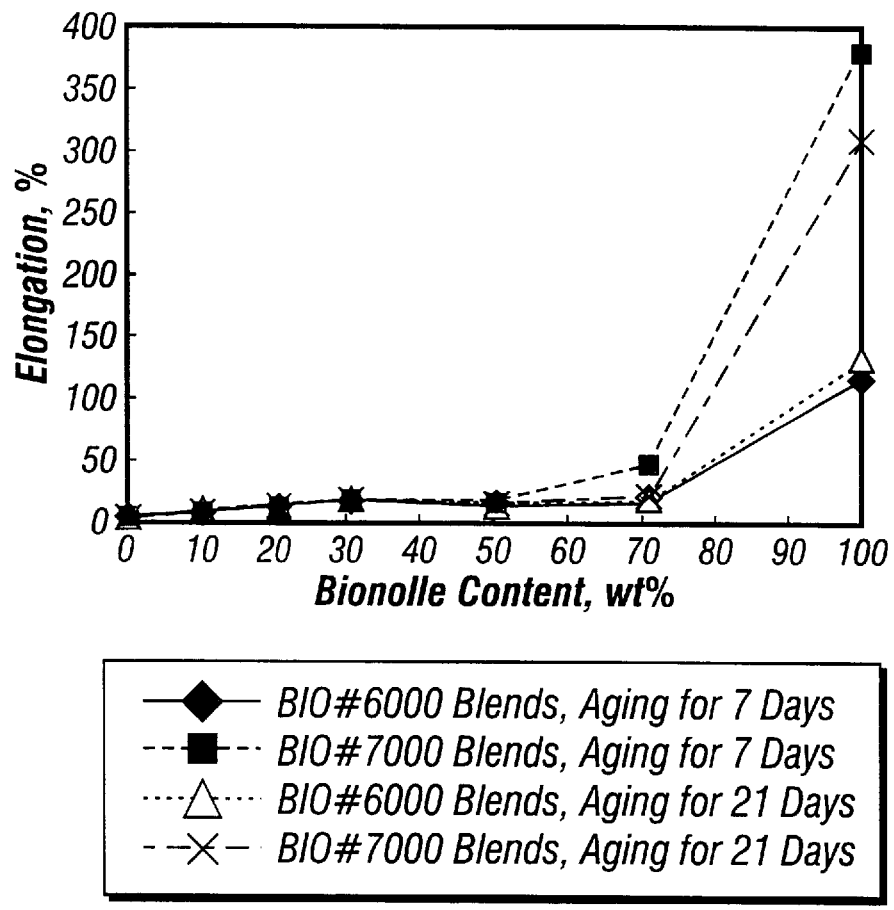
FIG. 8 is a graph showing percent elongation at yield and break of polylactic acid, BIONOLLE#6000, BIONOLLE#7000, and their blends.

Tensile properties (modulus and elongation at break) after aging for 7 and 21 days as a function of BIONOLLE#6000 and BIONOLLE#7000 content are shown in FIGS. 7 and 8. The modulus decreases (FIG. 7) and the elongation at break increases (FIG. 8) with increasing BIONOLLE#6000 and BIONOLLE#7000 content. As the aging time increases from 7 to 21 days, the modulus shows a slight increase (FIG. 7), and the elongation at break shows a slight decrease (FIG. 8). Since BIONOLLE#7000 is a softer polymer than BIONOLLE#6000, polylactic acid/BIONOLLE#7000 blends have a lower modulus and a higher elongation at break compared with those of polylactic acid/ BIONOLLE#6000 blends.

Unlike BIONOLLE#3000, BIONOLLE#6000 and BIONOLLE#7000 do not increase the elongation at break significantly when 10 to 40% by weight of BIONOLLE#6000 or BIONOLLE#7000 is blended with polylactic acid. This may be due to the fact that pure BIONOLLE#6000 and BIONOLLE#7000 do not possess the same tensile properties of BIONOLLE#3000, and also more importantly, the compatibility of polylactic acid with BIONOLLE#6000 and BIONOLLE#7000 is not as good as that of polylactic acid and BIONOLLE#3000. However, the compatibility of polylactic acid with BIONOLLE#6000 and BIONOLLE#7000 can be improved with the addition of a suitable compatibilizer, such as a small amount of BIONOLLE#3000.

Example 2

Aging Effect

The effect of aging on the blends was measured by physically aging the samples at room temperature and atmospheric pressure, and subsequently testing the samples by tensile testing according to ASTM D 882 with the modifications already stated above.

Figure 9:
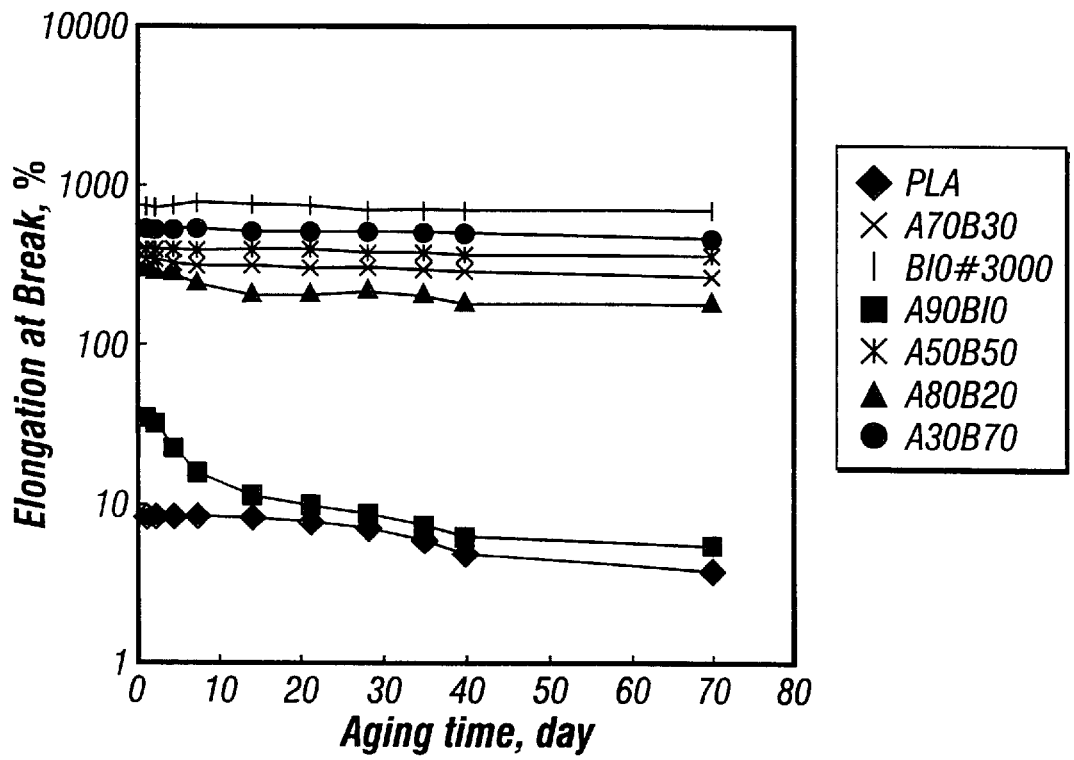
FIG. 9 is a graph showing percent elongation at break of polylactic acid, BIONOLLE#3000, and their blends as a function of aging.

FIG. 9 shows elongation at break of polylactic acid, BIONOLLE#3000, and their blends, as a function of aging. The elongation at break of polylactic acid was below 8%, and decreased to about 5% with aging. Similarly, the elongation at break of A90B10 was rather low (about 50%) and decreased to less than 10% with aging. However, blends having a BIONOLLE#3000 content of 20% or more by weight showed outstanding elongation at break (200% elongation for 20% BIONOLLE#3000, and similarly, 300% for 30%, 400% for 50%, and 500% for 70%, respectively). In addition, these BIONOLLE#3000 containing blends did not exhibit any significant reduction in elongation after aging.

Example 3

Biodegradation Testing in Soil

Soil testing in an artificial soil environment was performed on 0.3 mm thick films of the blends using the respirometric method developed at the NSF Biodegradable Polymer Research Center, University of Massachusetts Lowell and designated UML-7645. A standard soil mix (1:1:0.1 potting soil:sand:dehydrated cow manure by weight) was prepared and characterized. The soil test materials were exposed to the soil under controlled aerobic conditions at 30+±2° C. Carbon dioxide production, expressed as a fraction of the measured of theoretical carbon content of the test materials, was measured as a function of time. The degree of biodegradation of the test material is assessed by comparing the amount of $CO_2$ produced from the test material to that produced from a standard material, i.e., one that is known to biodegrade (here PLA was used for comparison).

Figure 10:
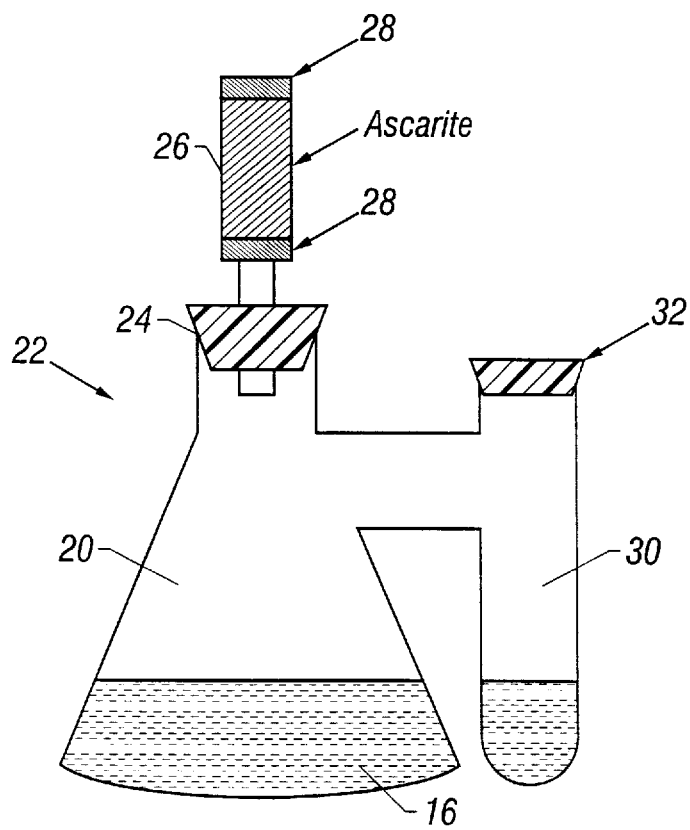
FIG. 10 is a schematic of a biometer for soil biodegradation testing.

Specifically, the soil biodegradation test was conducted as follows. Fifty grams (oven-dry weight basis) of soil was weighed into a large (14 cm) disposable weighing boat. Enough distilled water was added to the soil and mixed thoroughly to bring the soil to a moisture content of 60 to 70%. Approximately 15 g of the moist soil was set aside. The test specimen, or standard material, was added to the soil and the amended soil was mixed thoroughly. As shown in FIG. 10, the amended soil 16 was transferred to a large chamber 20 of a 250-mL biometer flask 22, packed to a uniform depth (about 2.5 cm), and covered by the 15 g of the moist soil set aside. The large chamber 20 was then closed with a rubber stopper 24 connected to a 3-mL plastic syringe 26 packed with a material 26 that removes any carbon dioxide from air entering the biometer during incubation, such as sodium hydroxide-coated silicon (e.g., Ascarite™), between plugs of a filter material 28, e.g., glass wool or cotton, that allows air, but not the Ascarite™, to pass.

The combined weight of the flask, rubber stopper, and amended soil containing the test specimen was determined and recorded. Twenty mL of 0.4M sodium hydroxide was pipetted into the side-arm chamber 30 of the biometer flask 22 and the side-arm chamber 30 was sealed with a rubber stopper 32. The biometer flask was placed in an environmental chamber at 30° C and this chamber was kept dark.

The carbon dioxide analysis was done by reacting the carbon dioxide produced in the biometer with the sodium hydroxide in the side-arm chamber to form an aqueous solution of sodium carbonate. The amount of carbon dioxide produced was monitored by removing the sodium hydroxide from the trap and transferring it to a glass test tube to which 5 mL of 1.5M barium chloride was added. The barium chloride reacts with the sodium carbonate to form a precipitate of barium carbonate. The amount of carbon dioxide evolved was calculated by standard stoichiometric calculation.

The net degradation was measured as the ratio of carbon dioxide evolved to the amount of theoretical maximum carbon dioxide production possible by the test specimen. The theoretical maximum carbon dioxide production was determined by the total organic carbon content of the test material (by calculation, if the chemical composition was well established, or elemental analysis). The maximum amount of carbon dioxide that can be theoretically evolved was calculated by the equation:

*Maximum carbon dioxide*=[($W{\times}C$)/100]${\times}$[44/12]

where W is the weight of the test specimen; C is the percent organic carbon in the test specimen, 44 is the molecular weight of carbon dioxide, and 12 is the equivalent weight of carbon.

The biodegradation testing in soil showed that the biodegradation rate of BIONOLLE#3000 by itself was extremely fast, while the biodegradation rate of polylactic acid by itself was relatively slow.

Figure 11:
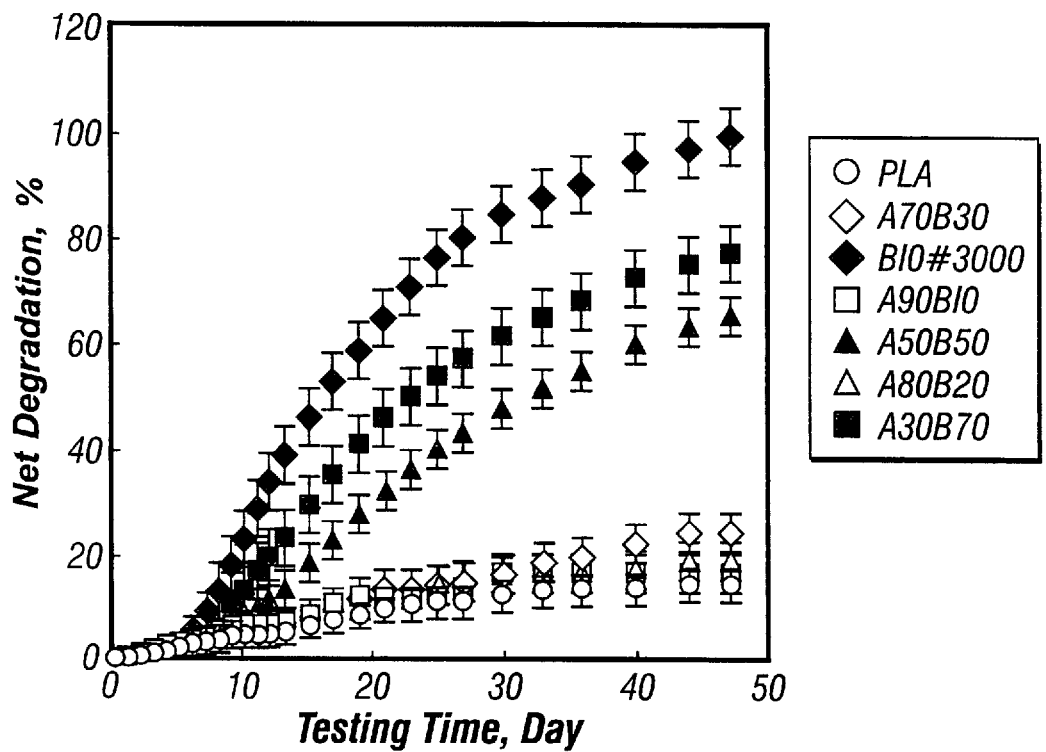
FIG. 11 is a graph showing net percent biodegradation of polylactic acid, BIONOLLE#3000, and their blends as a function of test time in soil.

The soil degradation testing results of the two polymers and their blends are reported in FIG. 11. After degradation for 45 days, BIONOLLE#3000 degraded almost 100%, while polylactic acid degraded only about 14% by loss in weight. For blends with 70 and 50% BIONOLLE#3000, the degradation rate was relatively fast. After 45 days, the A30B70, A50B50, and A70B30 blends degraded about 77%, 65% and 25%, respectively, by loss in weight. FIG. 11 shows that polylactic acid biodegrades in soil, but just not quickly, and the addition of the second aliphatic polymer, such as BIONOLLE#3000, increases the biodegradation rate.

The importance of the soil biodegradation curves shown in FIG. 11 is that a specific blend can now be designed such that this blend would have a certain net degradation in a given number of days within the soil.

Example 4

Biodegradation Testing in Compost

Biodegradation testing in an artificial compost environment was conducted on film samples in a simulated municipal compost. Biodegradation testing in an artificial compost environment was conducted on compression molded film samples of dimensions 20 mm×20 mm×0.3 mm in a simulated municipal compost mixture consisting of 60% by weight of water and the rest containing shredded leaves, shredded paper, mixed frozen vegetables, meat waste, urea, and commercial compost seeds. The carbon to nitrogen (C:N) ratio of the starting mix was 14:1. The composting process was carried out for 30 days at 55° C. Triplicate test samples were removed from the composting bioreactors at an interval of 5 days and weighed to measure the weight loss per surface area in the units of $\mu g/mm^2$.

After 20 days in the composting environment at 55° C., BIONOLLE#3000 had a high weight loss rate while polylactic acid had negligible weight loss. The weight loss rates in the blends of polylactic acid and BIONOLLE#3000 after 20 days in the composting environment were between the rates of polylactic acid and BIONOLLE#3000.

Figure 12:
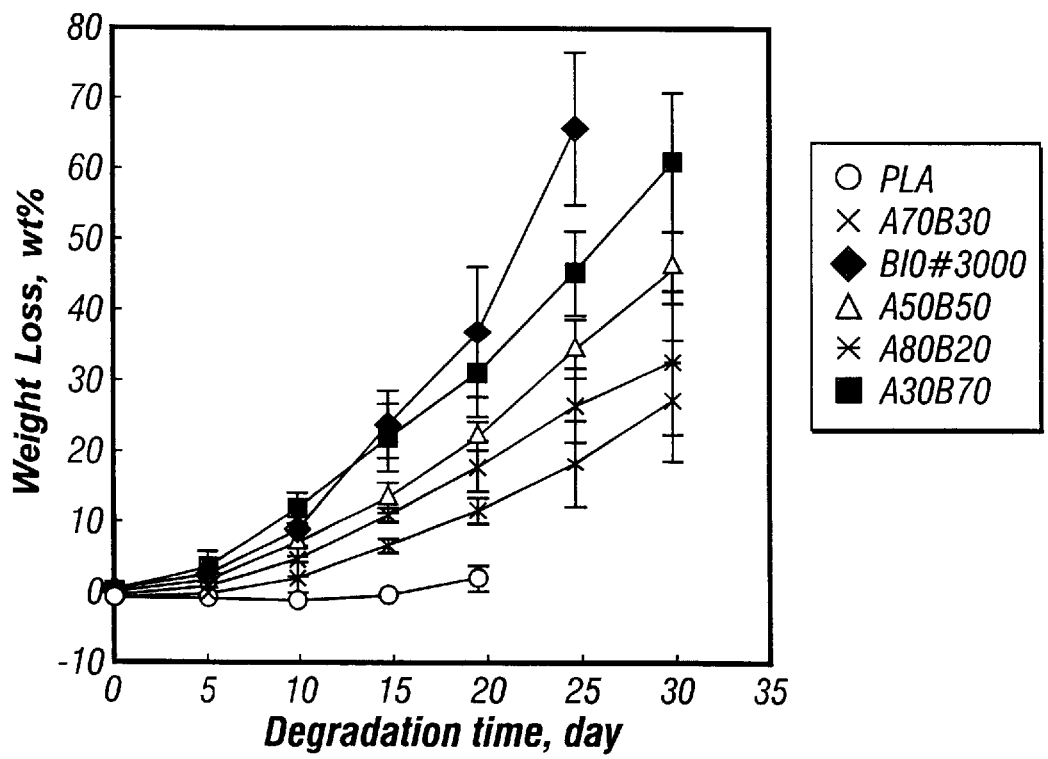
FIG. 12 is a graph showing net percent weight loss due to biodegradation of polylactic acid, BIONOLLE#3000, and their blends as a function of test time in compost.

The compost degradation testing results of the two polymers and their blends are reported in FIG. 12. After degradation for 20 days, BIONOLLE#3000 degraded almost 40%, while polylactic acid degraded only about 3%, by loss in weight. For blends with 70 to 20% BIONOLLE#3000, the degradation percentage was much greater (and the rate much faster) than that of polylactic acid, e.g., after 20 days, the A30B70, A50B50, and A70B30 blends degraded about 35%, 25% and 15%, respectively, by loss in weight. FIG. 12 shows that polylactic acid biodegrades in compost, but slowly, and the addition of even 20% by weight BIONOLLE#3000 increases this biodegradation rate dramatically.

The importance of the compost biodegradation curves shown in FIG. 12 is that a specific blend can now be designed such that this blend would have a certain net degradation in a given number of days in a composting environment.

Example 5

Morphology

Samples were analyzed by microscopy to investigate the morphology of the phases of polylactic acid versus the phases of BIONOLLE#3000. The blends were exposed to acetone to dissolve the polylactic acid component without affecting the BIONOLLE#3000 component. For the blend containing 70% by weight of polylactic acid and 30% by weight of BIONOLLE#3000, 67% of the material, or approximately 95% of the polylactic acid, was dissolved. The remaining material was in a sheet form, and the BIONOLLE#3000 phase in the original blend formed a continuous or co-continuous phase, while the dissolved polylactic acid left behind holes in the sheet-like structure of BIONOLLE#3000. This continuous or co-continuous structure of the BIONOLLE#3000 phase in the original blend explained the outstanding toughness shown in the graph of FIG. 6.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A biodegradable blend comprising:
   (a) a first polylactic acid-based polymer or copolymer, and
   (b) a second polymer consisting essentially of one or more polyesters,
   wherein said first and second polymers are present in a ratio of 9:1 to 1:9 by weight, and wherein the second polymer is a homopolymer or random copolymer that forms a continuous or co-continuous phase in the blend.

2. The biodegradable blend of claim 1, wherein said one or more polyesters are of one aliphatic $C_2$ to $C_{20}$ diacid or of a combination of two more different aliphatic $C_2$ to $C_{20}$ diacids.

3. The biodegradable blend of claim 1, wherein said first, polylactic acid-based polymer is a homopolymer of polylactic acid.

4. The biodegradable blend of claim 1, wherein said first, polylactic acid-based polymer is selected from the group consisting of D-polylactic acid, L-polylactic acid, D,L-polylactic acid, meso-polylactic acid, and any combination of D-polylactic acid, L-polylactic acid, D,L-polylactic acid and meso-polylactic acid.

5. The biodegradable blend of claim 1, wherein said first, polylactic acid-based polymer is a copolymer having at least 60% by weight of polylactic acid.

6. The biodegradable blend of claim 1, wherein said second polymer or copolymer is selected from the group consisting of polybutylenesuccinate homopolymer, polybutyleneadipate homopolymer, polybutylenesuccinate-adipate copolymer, polyethylenesuccinate homopolymer, polyethyleneadipate homopolymer and polyethylenesuccinate-adipate copolymer.

7. The biodegradable blend of claim 1, wherein said polyester is an aliphatic polyester.

8. The biodegradable blend of claim 1, wherein said second polymer or copolymer is a copolyester of an aliphatic polyester and up to 50 percent, by weight, of an aromatic polyester.

9. The biodegradable blend of claim 8, wherein said aromatic polyester is polyethylene terephthalate.

10. A biodegradable blend of claim 1, further comprising (c) a compatibilizer consisting essentially of one or more polyesters or polyvinyl alcohols.

11. The biodegradable blend of claim 1, said blend having an elongation at break of at least 10%.

12. The biodegradable blend of claim 1, said blend having an elongation at break of at least 200%.

13. The biodegradable blend of claim 1, said blend having an elongation at break of at least 10% after 70 days of aging.

14. The biodegradable blend of claim 1, said blend having an elongation at break of at least 200% after 70 days of aging.

15. The biodegradable blend of claim 1, said blend having a toughness of at least 10 MJ/m$^3$.

16. The biodegradable blend of claim 1, said blend having a toughness of at least 70 MJ/m$^3$.

17. The biodegradable blend of claim 1, wherein said second polymer is present in said blend as a co-continuous phase.

18. The biodegradable blend of claim 1, wherein said first, polylactic acid-based polymer or copolymer is a homopolymer of lactic acid or a block, graft, or random copolymer of lactic acid having the formula:

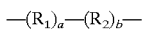

wherein $R_1$ is a lactic acid unit, $R_2$ is caprolactone, glycolide, trimethylene carbonate, dioxanone, butyryl lactone, or ethylene oxide, a is 10 to 10,000, and b is 0 to 10,000.

19. The biodegradable blend of claim 1, wherein said polyester has the formula:

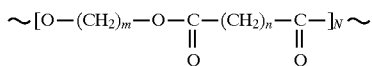

wherein m is 2 to 20, n is 2 to 20, and N is 10 to 10,000.

20. The biodegradable blend of claim 1, wherein said first, polylactic acid-based polymer or copolymer is a polylactic acid homopolymer, and wherein said second polymer or copolymer is a polybutylenesuccinate homopolymer.

21. The biodegradable blend of claim 1, wherein said first, polylactic acid-based polymer or copolymer is a polylactic acid homopolymer, and wherein said second polymer or copolymer is a polybutylenesuccinate-adipate copolymer.

22. A film comprising a biodegradable blend comprising:
(a) a first polylactic acid-based polymer or copolymer, and
(b) a second polymer consisting essentially of one or more polyesters,
wherein said first and second polymers are present in a ratio of 9:1 to 1:0 by weight, and wherein th second polymer is a homopolymer or random copolymer that forms a continuous or co-continuous phase in the blend.

23. A bag comprising a biodegradable blend comprising;
(a) a first polylactic acid-based polymer or co-polymer, and
(b) a Second polymer consisting essentially of one or more polyesters.
wherein said first and second polymers are present in a ratio of 9:1 to 1:0 by weight, and wherein the second polymer is a homopolymer or random copolymer that forms a continuous or co-continuous phase in the blend.

24. A container comprising a biodegradable blend comprising:
(a) a first polylactic acid-based polymer or copolymer, and
(b) a second polymer consisting essentially of one or more polyesters,
wherein said first and second polymers are present in a ratio of 9:1 to 1.0 by weight and wherein the second polymer is a homopolymer or random copolymer that forms a continuous or co-continuous phase in the blend.

25. A disposable diaper comprising a biodegradable blend comprising:
(a) a first polylactic acid-based polymer or copolymer, and
(b) a second polymer consisting essentially of one or more polyesters,
wherein said first and second polymers are present in a ratio of 9:1 to 1:0 by weight, and wherein the second polymer is a homopolymer or random copolymer that forms a continuous or co-continuous phase in the blend.

* * * * *

UNITED STATES PATENT AND TRADEMARK OFFICE
CERTIFICATE OF CORRECTION

| | |
|---|---|
| PATENT NO. | : 5,883,199 |
| APPLICATION NO. | : 08/825810 |
| DATED | : March 16, 1999 |
| INVENTOR(S) | : McCarthy et al. |

It is certified that error appears in the above-identified patent and that said Letters Patent is hereby corrected as shown below:

On the title page item (54), and col. 1, line 1, – replace "Polyactic" with -- Polylactic --

Signed and Sealed this

Twentieth Day of February, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,883,199 | Page 1 of 1 |
| APPLICATION NO. | : 08/825810 | |
| DATED | : March 16, 1999 | |
| INVENTOR(S) | : McCarthy et al. | |

It is certified that error appears in the above-identified patent and that said Letters Patent is hereby corrected as shown below:

Column 14, Claim 22, Line 4
Delete "1:0" and Insert --1:9--

Column 14, Claim 23, Line 15 (Approx)
Delete "1:0" and Insert --1:9--

Column 14, Claim 24, Line 27 (Approx)
Delete "1.0" and Insert --1:9--

Column 14, Claim 25, Line 39
Delete "1:0" and Insert --1:9--

Signed and Sealed this
Eighth Day of March, 2011

David J. Kappos
*Director of the United States Patent and Trademark Office*